United States Patent [19]

Ushikubo

[11] Patent Number: 5,254,311
[45] Date of Patent: Oct. 19, 1993

[54] CONTINUOUS MULTINOMINAL ANALYSIS METHOD AND APPARATUS

[75] Inventor: Masao Ushikubo, Tokyo, Japan

[73] Assignee: Olympus Optical Co., Ltd., Tokyo, Japan

[21] Appl. No.: 905,938

[22] Filed: Jun. 29, 1992

[30] Foreign Application Priority Data

Jul. 2, 1991 [JP] Japan .................. 3-161615

[51] Int. Cl.$^5$ .................. G01N 1/14; G01N 35/08
[52] U.S. Cl. .................. 422/81; 422/100; 422/105; 422/106; 422/107; 422/108; 436/43; 436/49; 436/50; 436/54; 436/55; 436/180; 73/864.21; 73/864.24
[58] Field of Search .................. 422/81, 63, 99, 100, 422/105, 106, 107, 108; 436/43, 50, 54, 149, 55, 174, 180; 73/864.21, 864.24

[56] References Cited

U.S. PATENT DOCUMENTS

| | | | |
|---|---|---|---|
| 3,929,411 | 12/1975 | Takano et al. | 422/81 |
| 4,326,851 | 4/1982 | Bello et al. | 422/63 |
| 4,448,752 | 5/1984 | Banno et al. | 422/81 |
| 4,451,433 | 5/1984 | Yamashita et al. | 422/63 |
| 4,615,866 | 10/1986 | Hyde et al. | 422/106 |
| 4,710,355 | 12/1987 | Ushikubo | 422/100 |
| 4,818,492 | 4/1989 | Shimizu | 422/100 |
| 4,844,870 | 7/1989 | Rasmussen et al. | 422/68 |
| 4,944,922 | 7/1990 | Hayashi | 422/100 |
| 4,970,468 | 11/1990 | Ishizawa et al. | 422/67 |
| 5,027,075 | 6/1991 | Harding, Jr. | 324/662 |
| 5,049,826 | 9/1991 | Sasao | 324/662 |

Primary Examiner—James C. Housel
Assistant Examiner—Long V. Le
Attorney, Agent, or Firm—Kenyon & Kenyon

[57] ABSTRACT

An automatic continuous multinominal analyzer comprises suction tubes to be inserted into vessels containing a reagent, each suction tube having a pair of electrode lines. The contacts of each pair of electrode lines are located above the suction port of the suction tube. Hence, the contacts are isolated from each other when the level of the reagent in a vessel is lower than the contacts, even if the reagent still remains in the vessel. If it is detected that the contacts in a vessel are isolated, this indicates that the vessel is almost empty. A display indicates a vessel which is almost empty on the basis of the result of the detection as to whether the contacts in the vessel are isolated. After a vessel is indicated on the display, the controller continues suction of the reagent and an analysis operation until the reagent in the indicated vessel is reduced to the minimum level which can be extracted through the suction tube. After the display indicates a vessel, the operator prepares to exchange the vessel with a new one filled with the reagent before the reagent in the vessel is reduced to the minimum level.

8 Claims, 3 Drawing Sheets

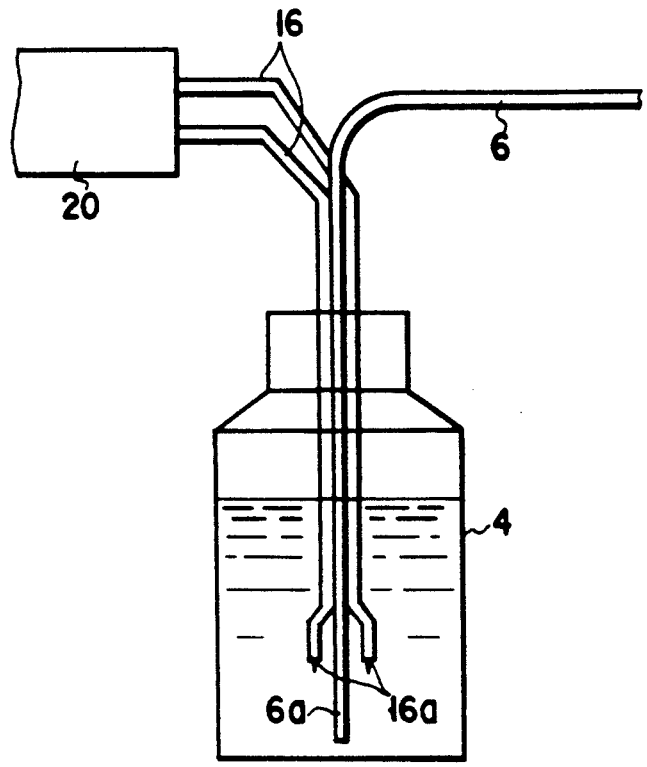
F I G. 2
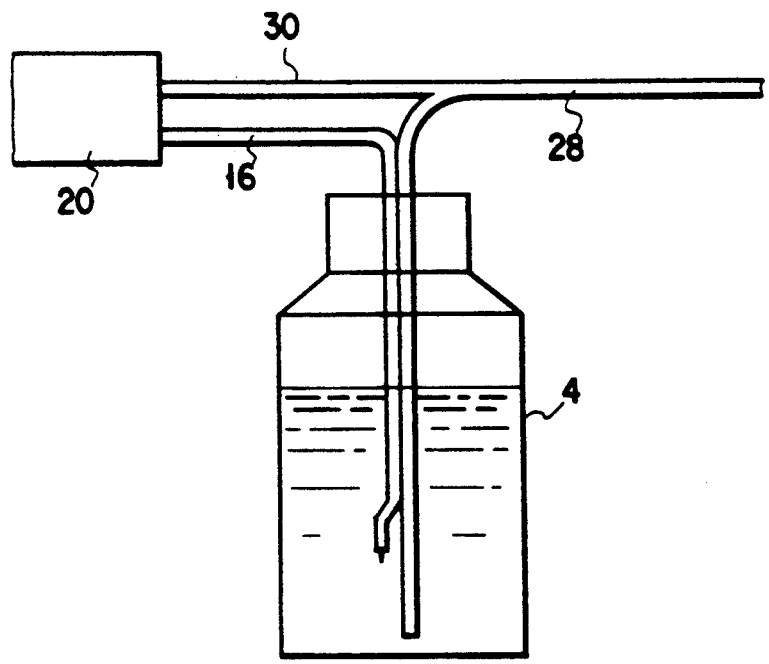
F I G. 3

CONTINUOUS MULTINOMINAL ANALYSIS METHOD AND APPARATUS

BACKGROUND OF THE INVENTION

1. Field of the Invention

This invention relates to a method and an apparatus for multinominal continuous analysis for raising multinominal reactions on a reaction line and analyzing the reactions.

2. Description of the Related Art

In an automatic continuous multinominal analyzer of discrete type, specimens to be analyzed and reagents for causing reaction with the specimens are supplied to reaction vessels. In general, since one reaction vessel corresponds to one item of analysis, the specimens are distributed to a plurality of reaction vessels to perform a plurality of items of analysis. The reaction vessels are arranged circumferentially and transferred intermittently to a reagent distributing position.

A plurality of reagent vessels containing reagents are positioned near the reagent distributing position.

The reagents in the reagent vessels are extracted by a suction tube and discharged to the reaction vessels by a discharge tube. Extraction and discharge operation is performed by a syringe. A common tube serving as a suction path and a discharge path for the syringe is selectively connected to the suction tube or the discharge tube by a switch valve.

When a reagent is to be extracted, the common tube is connected to the suction tube. A reagent of an amount necessary to the analysis is extracted by the suction operation of the syringe through the suction tube to the syringe.

Then, the common tube is connected to the discharge tube. The reagent is distributed to the reaction tubes through the discharge tube by the discharge operation of the syringe.

The degree of reaction of a specimen is detected as a density or an activation value by optically detecting the reacted specimen, when, for example, a color development reaction occurs.

In analysis by using an automatic analyzer of this type, generally, two reagents are used to analyze one item. Accordingly, reagents of the number twice the number of items of analysis are required. For example, if the number of items of analysis is twenty, forty kinds of reagents must be used. Hence, as the number of items of analysis is increased, the number of the reagent vessels is also increased; for example, several tens of reagents must be supplied to the automatic analyzer, and the management of the reagents is inevitably complicated. This is a disadvantage of the apparatus of this type.

The above-described automatic analyzer has another disadvantage that it is substantially impossible to exchange all the vessels at a time, since the amount of distribution varies depending on the item of analysis due to the variety of sizes of the reaction vessels. Therefore, the residual amounts of all of the reagents must be detected prior to an analysis.

The above-described automatic analyzer apparatus has still another disadvantage that, if the reagent in a reagent vessel is undesirably decreased to a little or nothing during an analysis, the common tube or suction tube may draw air, with the result that the reagent cannot be accurately distributed by the discharge tube. In addition, since a so-called drip-drip (the state that the discharge tube intermittently drips the reagent) occurs, results of the other items of analysis may be adversely affected. Further, if the outer surface of a reaction tube is contaminated, the reaction tube must be removed from the automatic analysis apparatus and cleaned prior to reanalysis, which may be required if analysis data is abnormal.

SUMMARY OF THE INVENTION

It is accordingly an object of the present invention to provide a method and an apparatus for continuous multinominal analysis which can detect that a residual reagent is reduced to a little, thereby preventing data abnormality due to drip-drip.

According to an aspect of the present invention, there is provided a multinominal analysis method for sucking liquid reagents contained in a plurality of vessels by sucking means, adding the liquid reagents to specimens and analyzing reactions of the specimens with the reagents, said method comprising the steps of:

determining first and second residual amounts of the liquid reagent in each of the vessels, the first residual amount corresponding to the minimum amount of reagent which the sucking means can suck, and the second residual amount corresponding to an amount slightly greater than the first residual amount;

sucking the liquid reagents contained in the vessels by the sucking means, adding the reagents to the specimens, thereby causing reaction of the specimens with the reagents, and analyzing the reactions;

detecting that the liquid reagent in each of the vessels is reduced to the second residual amount;

indicating on a display at least one of a liquid reagent which has been reduced to the second residual amount and the vessel containing the liquid reagent; and continuing analysis of the reactions until the liquid reagent which has been reduced to the second residual amount is further reduced to the first residual amount.

According to another aspect of the present invention, there is provided a multinominal analysis apparatus for sucking liquid reagents contained in a plurality of vessels, adding the liquid reagents to specimens and analyzing reactions of the specimens with the reagents, said apparatus comprising:

a plurality of sucking means corresponding to the plurality of vessels, for sucking the liquid reagents;

means for detecting that the liquid reagent in each of the vessels is reduced to a predetermined residual amount, the predetermined residual amount being slightly greater than a preset minimum amount of reagent which the sucking means can extract;

means for adding the liquid reagents sucked by said sucking means to the specimens, thereby causing reaction of the specimens with the regents;

means for analyzing the reactions of the specimens to which the liquid reagents are added;

means for indicating on a display at least one of a liquid reagent which has been reduced to the second residual amount and the vessel containing the liquid reagent; and means for continuing analysis of the reactions until the liquid reagent which has been reduced to the second residual amount is further reduced to the first residual amount.

The present invention is advantageous in that a reagent which has been reduced to a little and/or the vessel containing the reagent is indicated on a display, thereby calling the operator's attention to exchange the vessel with a new vessel filled with the reagent. In addition, reaction analysis is stopped, when the residual amount of the reagent in a vessel is reduced to a predetermined minimum level which can be sucked by the suction tube. Therefore, data abnormality due to intermittent drip of a reagent is prevented.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 2 is a side view showing details of the electrodes shown in FIG. 1;

FIG. 3 is a side view showing a portion of an analyzer according to a second embodiment of the present invention;

DETAILED DESCRIPTION OF THE PREFERRED EMBODIMENTS

Figure 1:
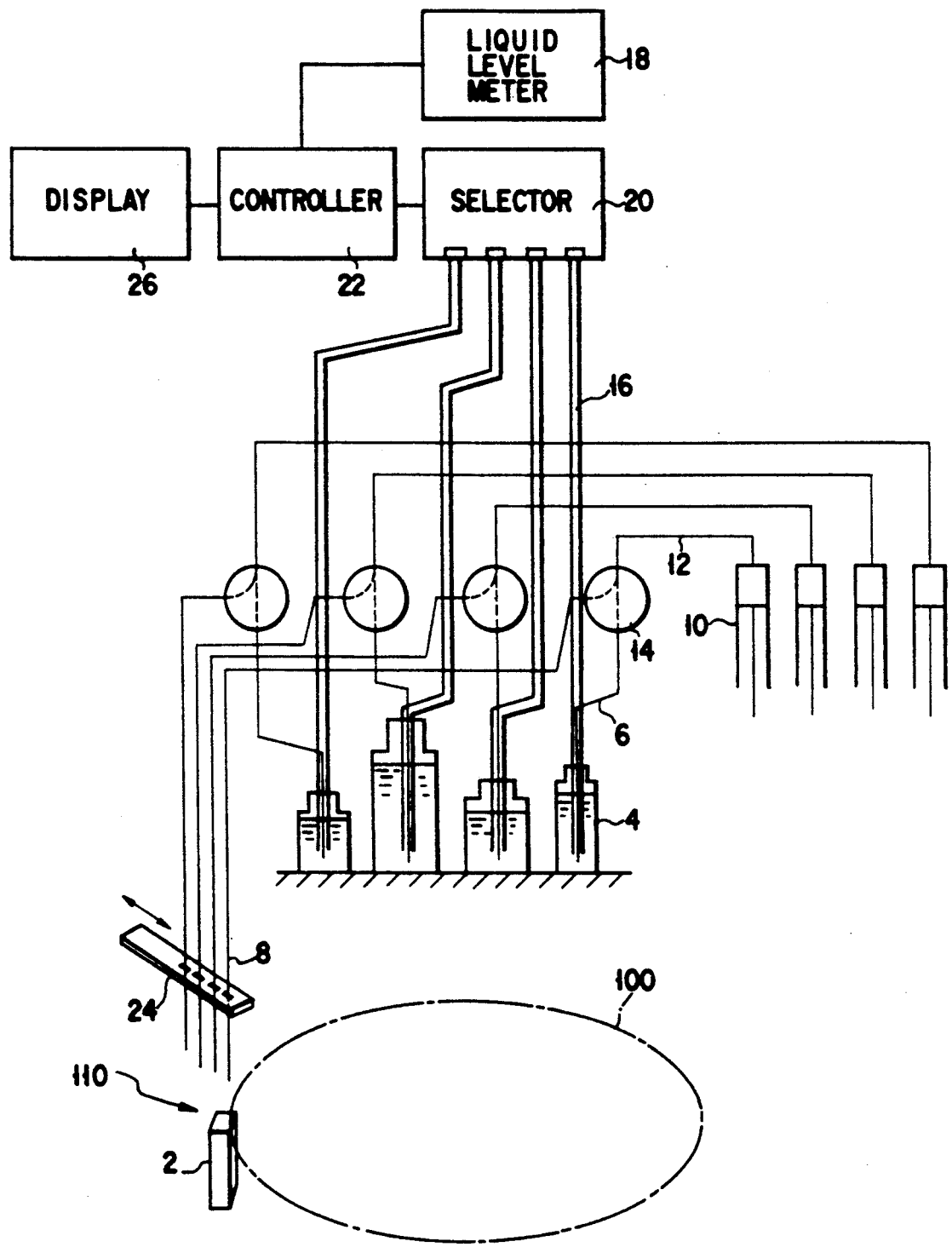
FIG. 1 is a schematic diagram showing an analyzer according to a first embodiment of the present invention.

FIG. 1 shows an automatic continuous multinominal analyzer of discrete type which allows a plurality of kinds of liquid specimens to be reacted on one reaction line.

A plurality of reaction vessels 2 (only one vessel is shown in FIG. 1) are filled with liquid specimens. The reaction vessels 2 are arranged along a circumferential reaction line 100 and transferred intermittently to a reagent distribution position 110.

A plurality of, for example, four vessels 4 filled with different reagents are placed near the reagent distribution position 110.

The distal ends of suction tubes 6 for extracting the reagents are immersed into the reagents in the respective vessels 4. Each of the distal ends of the suction tubes 6 has a pair of electrode lines 16 as indicated by the dot lines. The electrode lines 16 are made of platinum or stainless steel.

In each of the vessel 4, the pair of the electrodes 16 are electrically connected to a liquid level meter 18 via a selector 20. The selector 20 switches electrical connection between the liquid level meter and the electrode line pair 16, and allows only the selected pair of the electrodes 16 to be electrically connected to the liquid level meter 18. The switching operation of the selector 20 is controlled by a controller 22 such as a personal computer.

The liquid level meter 18 is electrically connected to the electrode line pair 16 in each vessel 4 via the selector 20, and detects the level of the reagent in the vessel 4 depending on whether the electrode lines are electrically connected to each other. Since electricity flows across the electrodes 16 within only a short period of time, i.e., several milliseconds, the reagent is not deteriorated.

The controller 22 includes a memory (not shown), which prestores the minimum volume of the reagent in each vessel 4 which the suction tube 6 can suck, i.e., the dead volume of the reagent which is detected immediately before drip-drip of the reagent through the discharge tube 8 occurs. The dead volume can be determined in accordance with the amount of the reagent which is distributed, depending on, for example, the volume of the vessel and the condition of analysis of the reagent.

As shown in FIG. 2, each electrode line 16 has a contact 16a at its distal end. The electrode line 16, excluding the contact 16a, is coated with Teflon (a trade name). The pair of the electrode lines 16 are welded to the suction tube 16 so as to sandwich the suction tube 16 made of Teflon.

In this embodiment, the contacts 16a are positioned with a suitable distance provided therebetween above a suction port 6a of the suction tube 6, such that they are isolated from each other when the liquid in the vessel is reduced to a predetermined level. The predetermined level of the liquid is set slightly higher than the liquid level corresponding to the dead volume.

The discharge tube 8 for discharging the reagent to the reaction tube 2 is positioned above the reaction tube 2. The discharge tube 8 is fixed to a plate 24. A plurality of tubes 8 (e.g., four tubes in FIG. 1) are selectively positioned at the reagent distributing position in accordance with the movement of the plate 24 as indicated by the allows. Reaction of the specimen in a reaction tube 2 with the reagent is detected by a sensor and analyzed by an analysis unit. Since the sensor and the analysis unit for this purpose are well known to those skilled in the art, they are not shown in the drawings or described in the specification.

Extraction and discharge of the reagent is performed by the operation of a syringe 10. A common tube 12 serving as a suction path and a discharge path for the syringe is selectively connected to the suction tube 6 or the discharge tube 8 by a switch valve 14.

When a reagent is to be extracted, the common tube 12 is first connected to the suction tube 6. A reagent of an amount necessary to the analysis is extracted by the suction operation of the syringe 10 and transferred from the vessel 4 through the suction tube 6 to the syringe 10.

Then, the common tube 12 is connected to the discharge tube 8. The reagent is distributed from the syringe 10 to the reaction tubes 12 through the discharge tube 8 by the discharge operation of the syringe 10.

The controller 22 switches the selector 20 in synchronism with the analysis period. As a result, the liquid level meter 18 obtains liquid level data for all of the vessels 4 in one cycle.

If the predetermined liquid level of a vessel 4 is detected, this indicates that the vessel 4 is almost empty. The controller 22 makes a display 26 to display indication corresponding to the vessel 4, thereby calling the operator's attention to exchange the vessel with a new one filled with the reagent. The indication may be displayed on the display 26 by any method, for example, the number of the vessel and/or the reagent contained in the vessel may be displayed.

When the reagent in the vessel is reduced to the predetermined liquid level, the reagent of an amount which can be sucked by the suction tube still remains in the vessel 4, as described above. Hence, even after the level of the reagent in the vessel reaches to the predetermined value, the controller 22 does not immediately stop the analysis but continues the analysis.

Then, the controller 22 determines whether the level of the reagent reaches the dead volume on the basis of the amount of the reagent which is sucked by the suction tube 6 after the level of the reagent is reduced to the predetermined liquid level. If it is determined that the reagent reaches the dead volume, the controller 22 stops the analysis.

Since it takes a time after the operator is cautioned by the display 26 before the analysis is stopped, the reagent is not wasted and the vessel can be exchanged timely and easily with a new one filled with the reagent.

In addition, since the vessel 4 in which the residual reagent is almost empty can be indicated on the display 26 and the analysis is automatically ceased, the suction tube 6 and the common tube 12 do not draw air. As a result, data abnormality due to drip-drip of the reagent is prevented and the reliability of the analysis result is increased.

FIG. 3 shows a second embodiment of the present invention. The second embodiment differs from the first embodiment merely in that a conductive plastic suction tube 28 is used in place of the suction tube 6 which is insulative. The tube 28 is connected to a selector 20 through a lead line 30. Since the tube 28 functions as an electrode line, one electrode line 16 suffices. In this embodiment, the same effect as in the first embodiment is obtained.

Figure 4:
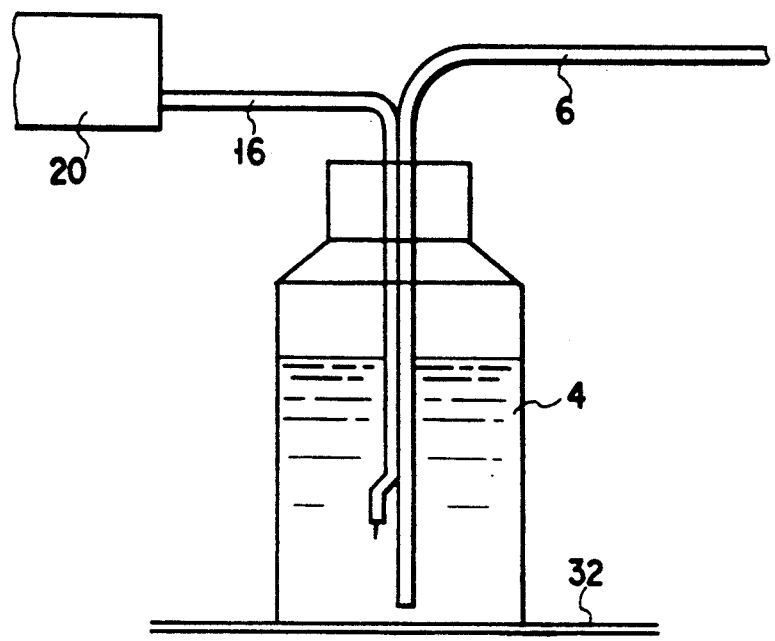
FIG. 4 is a side view showing a portion of an analyzer according to a third embodiment of the present invention.

FIG. 4 shows a third embodiment of the present invention. In this embodiment, the amount of the residual reagent in each vessel 4 is detected based on the electrostatic capacitance in the vessel 4. The vessels 4 are placed on a metal plate 32, and the amount of the residual reagent in each vessel is checked by detecting the electrostatic capacitance between the electrode line 16 and the metal plate 18. In this embodiment, only one electrode line 16 suffices and the suction tube 6 may be made of any material.

Figure 5:
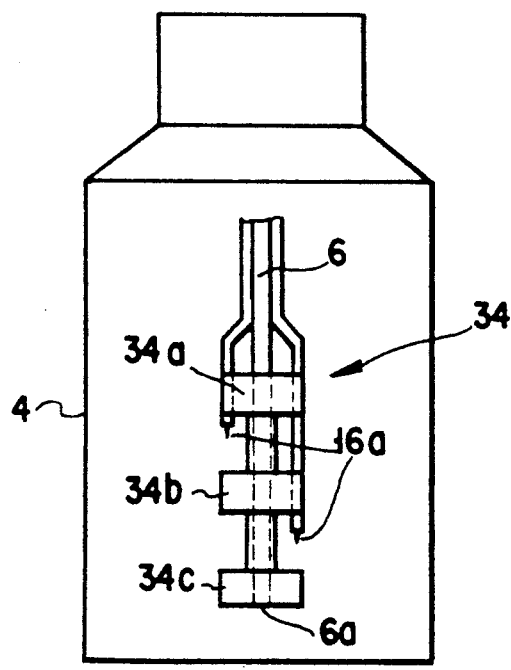
FIG. 5 is a side view showing a portion of an analyzer according to a fourth embodiment of the present invention.

FIG. 5 shows a fourth embodiment of the present invention. This embodiment is more reliable than the first embodiment since the malfunction of the liquid level meter is suppressed. As shown in FIG. 5, the distal end of the suction tube 6 is inserted into a tubular member 34 having rings to isolate the contacts 16a of the two electrode lines 16, one contacts being positioned above the other. Three rings 34a, 34b and 34c are provided on three portions of different levels of the tubular member 34 so as to protrude from the periphery of the member 34. The upper two rings 34a and 34b have grooves, in which the contacts 16a of the two electrodes are respectively positioned.

With this arrangement wherein the two contacts 16a are separated, they are isolated from each other when the level of the liquid reagent is lowered to a predetermined level, thereby increasing the reliability of the liquid level meter.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A multinominal analysis method for sucking liquid reagents contained in a plurality of vessels by sucking means, adding the liquid reagents to specimens and analyzing reactions of the specimens with the reagents, said method comprising the steps of:

(a) determining first and second residual amounts of the liquid reagent in each of the vessels, the first residual amount corresponding to a minimum amount of reagent which is to remain in each respective vessel so that the sucking means is capable of sucking reagent, and the second residual amount corresponding to an amount slightly greater than the first residual amount;

(b) sucking the liquid reagents contained in the vessels by the sucking means, adding the reagents to the specimens, thereby causing reaction of the specimens with the reagents, and analyzing the reactions;

(c) detecting that the liquid reagent in each of the vessels is reduced to the second residual amount;

(d) indicating on a display at least one of a liquid reagent which has been reduced to the second residual amount and the vessel containing the liquid reagent; and (e) continuing analysis of the reactions until the liquid reagent which has been reduced to the second residual amount is further reduced to the first residual amount.

2. A multinominal analysis apparatus for sucking liquid reagents contained in a plurality of vessels, adding the liquid reagents to specimens and analyzing reactions of the specimens with the reagents, said apparatus comprising:

a plurality of sucking means corresponding to the plurality of vessels, for sucking the liquid reagents;

mans for storing a value corresponding to a minimum amount of each of the liquid reagents in the vessels, said minimum amount of each reagent corresponding to a first residual amount of reagent which is to remain in each respective vessel so that the sucking means is capable of sucking reagent;

means for detecting that the liquid reagent in each of the vessels is reduced to a predetermined second residual amount, the predetermined second residual amount being slightly greater than the first residual amount;

means for adding the liquid reagents sucked by said sucking means to the specimens, thereby causing reaction of the specimens with the reagents;

means for analyzing the reactions of the specimens to which the liquid reagents are added;

means for indicating on a display at least one of a liquid reagent which has been reduced to the second residual amount and the vessel containing the liquid reagent; and means for continuing analysis of the reactions until the liquid reagent which has been reduced to the second residual amount is further reduced to the first residual amount.

3. An analysis apparatus according to claim 2, wherein said detecting means detect the level of the liquid reagent in each vessel, thereby indicating the residual amount of the reagent.

4. An analysis apparatus according to claim 3, wherein said detecting means include a pair of electrodes which are to be respectively inserted in the vessels.

5. An analysis apparatus according to claim 4, wherein said sucking means include a suction tube serving as one of the electrodes.

6. An analysis apparatus according to claim 4, wherein the distal end of one of the electrodes is isolated from that of the other electrode one distal end being positioned above the other.

7. An analysis apparatus according to claim 2, wherein said detecting means detect the electrostatic capacitance of each vessel, thereby detecting the residual amount of liquid reagent in the vessel.

8. An analysis apparatus according to claim 7, wherein said detecting means include a conductive material placed under the vessel and an electrode which is to be inserted into a vessel.

* * * * *

UNITED STATES PATENT AND TRADEMARK OFFICE
CERTIFICATE OF CORRECTION

PATENT NO. : 5,254,311
DATED : October 19, 1993
INVENTOR(S) : Masao USHIKUBO

It is certified that error appears in the above-indentified patent and that said Letters Patent is hereby corrected as shown below:

Column 4, line 38, change "allows" to --analysis."

Column 5, line 7, between "reaches" and "the" delete "to".

Column 5, line 23, change "ceased" to --discontinued--.

Column 5, line 53, change "contacts" to --contact--.

Column 6, line 67, change "indicating" to --detecting--.

Column 8, line 1, after "electrode" insert a comma.

Signed and Sealed this

Fourteenth Day of June, 1994

Attest:

BRUCE LEHMAN

*Attesting Officer*     *Commissioner of Patents and Trademarks*